(12) United States Patent
Tran-Guyon et al.

(10) Patent No.: US 7,994,215 B2
(45) Date of Patent: Aug. 9, 2011

(54) HIGH PURITY PHTHALEIN DERIVATIVES AND METHOD FOR PREPARING SAME

(75) Inventors: Joanne Tran-Guyon, Montigny le Bretonneux (FR); Francois Scherninski, Paris (FR)

(73) Assignee: Patent-Pharma, Paris (FR)

( * ) Notice: Subject to any disclaimer, the term of this patent is extended or adjusted under 35 U.S.C. 154(b) by 39 days.

(21) Appl. No.: 12/397,936

(22) Filed: Mar. 4, 2009

(65) Prior Publication Data

US 2010/0179334 A1 Jul. 15, 2010

Related U.S. Application Data

(63) Continuation of application No. 10/533,377, filed as application No. PCT/FR03/03205 on Oct. 28, 2003, now Pat. No. 7,518,002.

(30) Foreign Application Priority Data

Oct. 29, 2002 (FR) .................................... 02 13528

(51) Int. Cl.
*A61K 31/352* (2006.01)
*C07D 307/94* (2006.01)
(52) U.S. Cl. ...................... 514/453; 549/344
(58) Field of Classification Search .................. 514/453; 549/344

See application file for complete search history.

(56) References Cited

U.S. PATENT DOCUMENTS

| 1,931,049 A | 10/1933 | Woods et al. |
| 1,965,842 A | 7/1934 | Kranz |
| 5,637,733 A | 6/1997 | Sujeeth |
| 6,514,700 B1 * | 2/2003 | Singh ................................ 435/6 |

FOREIGN PATENT DOCUMENTS

| DE | 136 498 | 11/1979 |
| DE | 360 691 C | 10/1992 |

OTHER PUBLICATIONS

R.C. Gibbs, "The Absorption Spectra of Some Phthaleins of the Trihydroxyphenols" *J. Am. Chem. Soc.* vol. 51 pp. 1755-1766 (1929).
Shawn C. Burdette et al., "Fluorescent Sensors for Zn2+ Based on a Fluorescein Platform: Synthesis, Properties and Intracellular Distribution" *J. Am. Chem. Soc.*, vol. 123, pp. 7831-7841 (2001).
M.A. Matveets, et al., "Study of Spectrophotometric and Luminescence Properties of Hydroxyxanthene Dyes in Aqueous Solution" *Zhurnal Analiticheskoi Khimii*, vol. 34, No. 6, pp. 1049-1054 (1979). Database CA 'Online! Chemical Abstracts Service, Columbus, Ohio, US: XP002248842 accession No. STN Database accession No. 91:124850 abstract (1979).

* cited by examiner

*Primary Examiner* — Taofiq A Solola
(74) *Attorney, Agent, or Firm* — Buchanan Ingersoll & Rooney P.C.

(57) ABSTRACT

High purity phthalein derivatives are useful for medical applications and/or in the field of biotechnology. The phthalein derivatives are prepared by a method whereby a phthalic anhydride derivative is condensed with a naphthol or phenol derivative in an organic acid ester and the crystals of the resulting condensate are converted by action of a strong acid or one of its precursors in anhydrous medium.

18 Claims, 3 Drawing Sheets

Radiocrystallography of the crude fluorescein

Radiocrystallography of the fluorescein after conversion with acid (yellow)

Radiocrystallography of the crude 4',5'-dimethylfluorescein

Radiocrystallography of the 4',5'-dimethylfluorescein after conversion with acid Radiocrystallography of the crude 4',5'-dihydroxyfluorescein Radiocrystallography of the 4',5'-dihydroxyfluorescein after conversion with acid

HIGH PURITY PHTHALEIN DERIVATIVES AND METHOD FOR PREPARING SAME

PRIORITY

This application is a continuation of U.S. Ser. No. 10/533,377, filed Nov. 22, 2005 now U.S. Pat. No. 7,518,002 as the National Stage of International Application No. PCT/FR2003/003205, filed Oct. 28, 2003, which claims the benefit of France Patent Application Serial No. 02/13,528, filed on Oct. 29, 2002. The contents of both applications are hereby incorporated by reference in their entireties.

Phthaleins are molecules having the following xanthene unit:

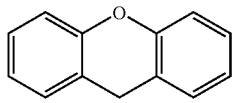

These products are useful as dyes in various industries, in particular the textile industry, the paper industry, printing, reprography, the food industry, the cosmetics industry and the pharmaceutical industry. Phthaleins are, currently, the subject of a considerable resurgence of interest in the health field, for their diagnostic use, in particular in the context of medical imaging and in the field of the biotechnology for labeling biological molecules (nucleic acids, proteins, lipoproteins, membrane lipids) and following the intracellular or extracellular biochemical activity of biological molecules.

For example, fluorescein is a phthalein commonly used in opthalmology for performing retinal angiography by fluorescence. The diagnostic advantage of fluorescein angiography is currently increased by the appearance of new medicinal products for treating vascular pathologies of the retina and of the choroid and the availability of a new generation of retinographs that make it possible to perform digital fluorescence imaging that has higher performance levels and gives greater resolution than the former systems of acquisition on photographic emulsions.

In parallel, the quality and safety requirements of the new international pharmaceutical standards (ICH: International Commission of Harmonization, ICH Q Topic Q3A 1999) have considerably increased. The same is true with regard to the use of phthaleins in biotechnologies that require reagents of increasingly high quality. In order to satisfy the current requirements, the level of purity of the phthaleins used in the pharmaceutical field or that of biotechnology must necessarily be very high. By way of example, in the publication "Effective differences in the formulation of intravenous fluorescein and related side effects", Am. J. Opthalmol. 78, 2: 217-221, 1974, L. Yannuzzi showed a correlation between the purity of phthaleins, in particular that of fluorescein, and the tolerance of these substances when they are administered to humans by injection.

The high purity phthaleins according to the invention have the general formula (I):

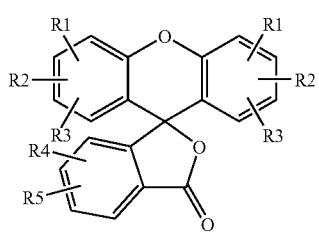

in which R1, R2, R3, R4 and R5, which are identical to or different from one another, are chosen from the group comprising the following radicals or groups: hydrogen, hydroxyl, halogen, acetyl, amino, phosphate, nitro, sulfonate, carboxyl, alkylcarboxyl having from 2 to 30 carbon atoms, alkyl having from 1 to 30 carbon atoms, cycloalkyl having from 3 to 12 carbon atoms, alkyloxy having from 1 to 30 carbon atoms, haloalkyl having from 1 to 30 carbon atoms, hydroxyalkyl having from 1 to 30 carbon atoms, alkyl ester having from 2 to 40 carbon atoms, nitroalkyl having from 1 to 30 carbon atoms, carboxyalkyl having from 2 to 30 carbon atoms, aminoalkyl having from 1 to 30 carbon atoms, sulfoalkyl having from 1 to 30 carbon atoms, aryl, aryloxy, arylalkyl, haloaryl, aryl ester, succinimidyl ester, isothiocyanate, maleimide, iodoacetamide, haloacetamide, chlorosulfonic, purine or pyrimidine bases, monosaccharides, preferably hexoses or pentoses, oligosides and polyosides, polypeptides, proteins and phospholipids, R1 and R5 are not hydrogen when R1 is a group —CH$_2$—CH$_2$—COOH, R2 is a hydroxyl group and R4 is a group —COOH, these phthaleins containing no more than 1% by weight, preferably no more than 0.5% by weight, and even more preferably not more than 0.2% by weight, of residual impurities.

A phthalein that is particularly advantageous, in particular for ophthalmic applications, is fluorescein having such a purity.

It is known practice to prepare the phthaleins of formula (I) by the condensation of a phthalic anhydride derivative with a phenol derivative having a free ortho-position with respect to a hydroxyl group.

This condensation is carried out by heating at the melting temperature of a mixture of the phthalic anhydride and of the phenol derivative, in the desired proportions.

This condensation can optionally be carried out in a dilution solvent. It can also be carried out in the presence of a catalyst.

In the absence of solvent, during the heating, the reaction medium rapidly thickens and has a tendency to harden. Within the reaction medium, areas where the temperature is too high and areas where the temperature is not high enough then form.

In the areas where the temperature is too high, the reactants and/or the reaction product are degraded and, in the areas where the temperature is not high enough, the reaction is not complete. The product obtained is of mediocre quality since it contains by-products that are very difficult to remove.

In order to improve this known method, the addition of an inert solvent or the use of a catalyst has been considered.

Thus, U.S. Pat. No. 1,931,049 describes the addition to the reaction medium of an inert solvent consisting of a benzene-based or aliphatic hydrocarbon, more particularly ortho-dichlorobenzene. However, the condensation reaction is then incomplete, and generate intermediate products that are subsequently difficult to remove. Therefore the method described in U.S. Pat. No. 1,931,049 does not make it possible to obtain a high purity phthalein according to the definition of the present application. Moreover, higher aliphatic hydrocarbons are not miscible with the reaction medium; consequently, they introduce no improvement in terms of thermal transfer and impair the elimination of the water formed, thereby slowing down the reaction, which takes place exclusively in a hydrophobic medium.

Regarding the catalysts that are used to improve the reaction yield, these are concentrated sulfuric acid, anhydrous zinc chloride and tin chloride.

The German patent DE 360691, describes the use of an aromatic sulfonic acid as a catalyst, in particular benzenesulfonic acid, alone or combined with one of the abovementioned three catalysts.

It so happens, however, that the addition of these catalysts leads to a reaction product that sets and hardens with entrapment of impurities, which can no longer be eliminated from the desired product.

In order to eliminate both the generated by-products and the impurities, isolation and purification methods have been developed, but none have made it possible to substantially improve the quality of phthaleins.

A conventional method consists in basifying the phthalein in an aqueous medium so as to dissolve it, and then in acidifying it so as to allow it to precipitate. These two steps are repeated successively in an attempt to eliminate the impurities. However, this method does not bring about a noticeable improvement in the purity of the product since, while the impurities dissolve with the phthalein during the basifying step, they precipitate again with the phthalein during the acidification step. In addition, this purification method has the drawback of producing a considerable amount of salts which are difficult and expensive to subsequently eliminate.

U.S. Pat. No. 1,965,842 describes the purification of phthaleins, derived from hydroxybenzene, by direct extraction of the by-products with dichlorobenzene alone or in a mixture with other solvents. This direct extraction of the crude product with the solvent in question does not, however, make it possible to obtain extensive elimination of impurities, which remain partly trapped in the phthalein crystals.

None of the purification methods described in the prior art makes it possible to reach a level of purity that is sufficient to allow the pharmaceutical use of phthaleins.

Given the advantage of these molecules for medical diagnosis, the production of high purity phthaleins is a real medical need and would satisfy a high demand, in particular for pharmaceutical applications in opthalmology, for diagnosis, in particular in medical imaging, or in the field of biotechnological applications (for example, as dye to label molecules).

The inventors have, to their credit, at the end of extensive research, found that it is possible to obtain high purity products by the condensation of a phthalic anhydride with a phenol or naphthol derivative in a specific solvent which consists of an organic acid ester.

They have also found that the use of organic acid esters as solvents makes it possible to carry out this condensation with an excellent yield, greater than 75%.

Specifically, these solvents have the particularity
firstly, of leading to specific crystallization of the phthalein that derives from the condensation and of excluding, from the generated crystals, all the impurities that remain dissolved in the reaction medium, and
secondly, of allowing a complete condensation that is predominant, to detrimental and unwanted side reactions, which results in the total consumption of the reactants and minimizes the formation of by-products.

The method in accordance with the invention thus makes it possible to obtain high purity phthaleins with a yield that is satisfactory from an industrial point of view.

DETAILED DESCRIPTION OF THE INVENTION

Figure 1:
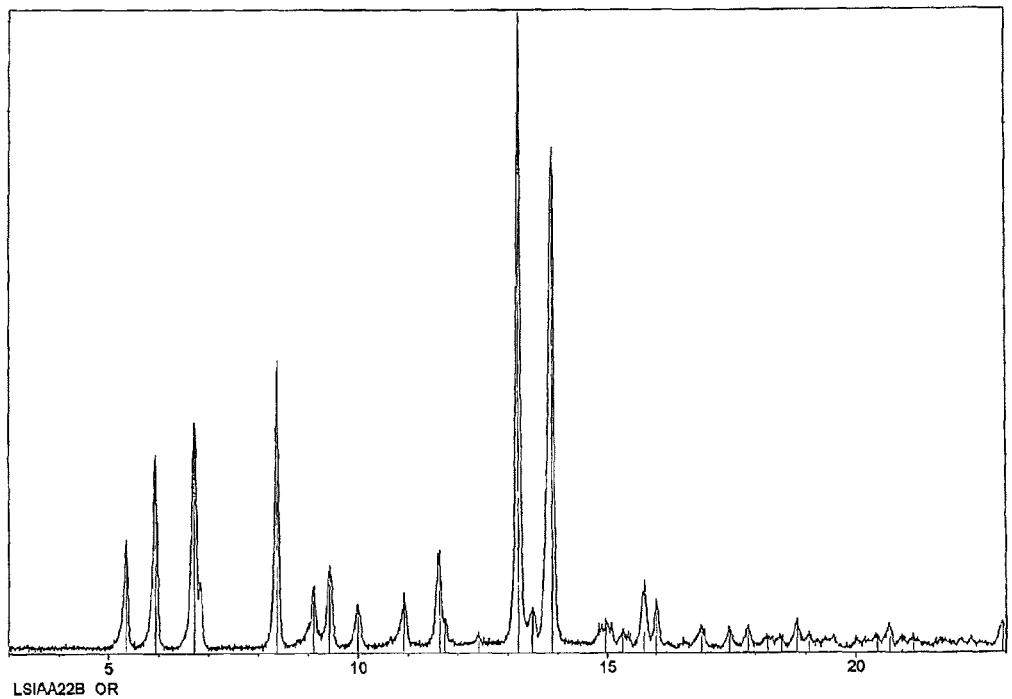
FIG. 1 is a radiocrystallography spectrum of crude fluorescein.

More particularly, the invention is related to a method for preparing phthaleins, from which the residual impurities have been removed, having general formula (I):

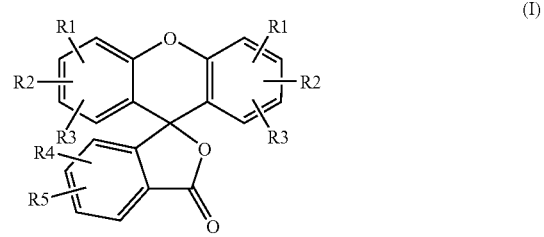

(I)

in which R1, R2, R3, R4 and R5, which are identical to or different from one another, are chosen from the group comprising the following radicals or groups: hydrogen, hydroxyl, halogen, acetyl, amino, phosphate, nitro, sulfonate, carboxyl, alkylcarboxyl having from 2 to 30 carbon atoms, alkyl having from 1 to 30 carbon atoms, cycloalkyl having from 3 to 12 carbon atoms, alkyloxy having from 1 to 30 carbon atoms, haloalkyl having from 1 to 30 carbon atoms, hydroxyalkyl having from 1 to 30 carbon atoms, alkyl ester having from 2 to 40 carbon atoms, nitroalkyl having from 1 to 30 carbon atoms, carboxyalkyl having from 2 to 30 carbon atoms, aminoalkyl having from 1 to 30 carbon atoms, sulfoalkyl having from 1 to 30 carbon atoms, aryl, aryloxy, arylalkyl, haloaryl, aryl ester, succinimidyl ester, isothiocyanate, maleimide, iodoacetamide, haloacetamide, chlorosulfonic, purine or pyrimidine bases, monosaccharides, preferably hexoses or pentoses, oligosides and polyosides, polypeptides, proteins and phospholipids, R1 and R5 are not representing hydrogen when R1 is a group —$CH_2$—$CH_2$—COOH, R2 is a hydroxyl group and R4 is a group —COOH, by condensation of a phthalic anhydride derivative Of formula (II) with a phenol or naphthol compound of formula (III)

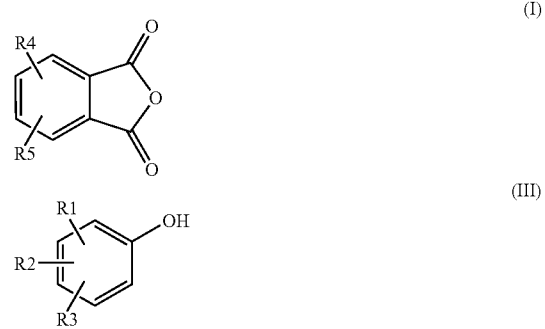

(I)

(III)

in which R1, R2, R3, R4 and R5 have the same meanings as above,
in a solvent consisting of an organic acid ester.

Advantageously, the starting compound (III), which is condensed with the phthalic anhydride (II), is chosen from the group comprising in particular resorcinol, orcinol, naphthol, pyrogallol, alkylaminophenol and arylaminophenol.

When resorcinol is used as starting product, the method in accordance with the invention makes it possible to prepare fluorescein.

Advantageously, the solvent used in the method in accordance with the invention is an organic acid ester of formula (IV)

in which $R_6$ is chosen from the group comprising the following radicals or groups: hydrogen, alkyl having from 1 to 30 carbon atoms, cycloalkyl having from 3 to 12 carbon atoms, haloalkyl having from 1 to 30 carbon atoms, hydroxyalkyl having from 1 to 30 carbon atoms, nitroalkyl having from 1 to 30 carbon atoms, aryl, aryloxy, alkylaryl, arylalkyl, substituted arylalkyl, haloaryl, aryl ester, alkyl ester having from 2 to 40 carbon atoms, and alkyloxy having from 1 to 30 carbon atoms, $R_7$ representing one of the following groups: alkyl having from 1 to 30 carbon atoms, cycloalkyl having from 3 to 12 carbon atoms, haloalkyl having from 1 to 30 carbon atoms, hydroxyalkyl having from 1 to 30 carbon atoms, nitroalkyl having from 1 to 30 carbon atoms, aryl, aryloxy, alkylaryl, arylalkyl, substituted arylalkyl, haloaryl, aryl ester, alkyl ester having from 2 to 40 carbon atoms, or alkyloxy having from 1 to 30 carbon atoms.

Particularly advantageously, the abovementioned solvent is chosen from the group comprising methyl, ethyl, propyl or butyl benzoates, methyl, ethyl, propyl or butyl heptanoates, methyl, ethyl, propyl or butyl octanoates, methyl, ethyl, propyl or butyl laurates, methyl, ethyl, propyl or butyl myristates and methyl, ethyl, propyl or butyl palmitates, and mixtures thereof.

The solvent is chosen according to its boiling point, so as to make it possible to carry out the condensation reaction at a temperature of between 150° C. and 250° C.

The condensation reaction can be carried out at atmospheric pressure or under a pressure that is adjusted according to the difference that exists between the temperature corresponding to the boiling point of the solvent and the temperature necessary to carry out the reaction, in particular under a pressure greater than atmospheric pressure when the boiling point of the compound (IV) is lower than the reaction temperature.

The condensation reaction can be carried out in the presence of a catalyst chosen from the group comprising in particular Lewis acids, such as $ZnCl_2$ or $AlCl_3$, Brönsted acids such as $H_2SO_4$, polyphosphoric acid, or salts thereof.

Advantageously, the catalyst used is an alkali metal salt of hydrogen sulfate. Particularly advantageously, the catalyst used is potassium hydrogen sulfate ($KHSO_4$) or sodium hydrogen sulfate. The use of hydrogen sulfate as catalyst makes it possible to obtain an excellent yield for the condensation reaction and has the advantage, unlike other catalysts, of making it possible to obtain complete condensation of the reactants, of being able to be completely eliminated from the phthalein obtained, and of not inducing the formation of tars in the reaction medium.

At the end of the condensation reaction, a crude product is obtained, the organic purity of which is already much higher than that of the products obtained with the methods of the prior art, since it is equal to or greater than 95%.

However, this purity is not yet sufficient to allow pharmaceutical use, in particular by injection. Furthermore, as shown above, the purification methods described in the prior art do not result in a process that makes it possible to notably improve this purity.

At the end of extensive research, surprisingly and unexpectedly, the inventors have found a method that considerably increases the purity of crude phthaleins resulting from the condensation reaction, by treating them with a strong acid or one of its precursors in an anhydrous organic medium.

According to an advantageous embodiment, the method in accordance with the invention consequently comprises, after the condensation reaction, a step consisting in acidifying the product resulting from the condensation, in an anhydrous organic medium, by addition of a strong acid or one of its precursors, chosen from the group comprising in particular sulfuric acid, hydrochloric acid, hydrobromic acid, hydrofluoric acid, hydriodic acid, polyphosphoric acid, pyrophosphate ($P_2O_5$), and mixtures thereof. This acidification is carried out until the phthalein crystals resulting from the condensation are converted to phthalein crystals having a different structure.

The effect of this acidification step is to convert the crude phthalein that is insoluble and dispersed in the organic medium into a form that has a different crystalline structure and is slightly soluble in this same medium. This conversion is very rapid, and takes place via an intermediate solubilization phase during which the impurities are released and completely eliminated from the phthalein crystals. This new purification method is very advantageous since it requires very little solvent and yields to a very high purity in a very short time.

According to the method of the present invention, this purification step is carried out by dispersing the crude phthalein resulting from the condensation, in an anhydrous solvent, preferably in an alcohol, a ketone, an ether or a halogenated solvent, that is either used alone or as a mixture, even more preferably in absolute ethanol or acetone, alone or as a mixture.

The dispersion of crude phthalein thus obtained is acidified by the addition of a strong acid or one of its precursors, chosen from the group comprising in particular sulfuric acid, hydrochloric acid, hydrobromic acid, hydrofluoric acid, hydriodic acid, polyphosphoric acid, pyrophosphate ($P_2O_5$), and mixtures thereof.

According to a particularly advantageous embodiment, the acidification is carried out either by sparging gaseous hydrochloric acid into the phthalein dispersion, or by adding hydrochloric acid dissolved beforehand in an organic solvent.

According to another advantageous embodiment of the method in accordance with the invention, the product obtained after acidification is washed with a washing solution chosen from the group comprising water, polar solvents such as alcohols or ketones, or slightly polar solvents such as ethers and halogenated solvents, used pure or as a mixture.

At the end of the purification step, the phthaleins thus treated have a purity of greater than 98%, preferably greater than 99%, more preferably greater than 99.5%, and even more preferably of 99.8%.

The phthaleins thus obtained have the suitable quality to prepare other phthaleins of formula (I) by chemical modification of the groups R1, R2, R3, R4 and R5 according to the conventional methods of the art, in particular to obtain phthaleins that can be used for labeling biological molecules (nucleic acids, proteins, lipoproteins, membrane lipids) and in the field of biotechnological applications (for example, for the labeling of molecules and of their intracellular or extracellular biochemical activity).

The invention is particularly suitable for preparing very high purity fluorescein, i.e. such that its content of each of the by-products of the reaction is less than or equal to 0.2%, and preferably less than or equal to 0.1%, the sum of the contents of each of these by-products being less than or equal to 0.5%.

The method for preparing a fluorescein having the above-mentioned purity comprises the following successive steps:
- condensing phthalic anhydride with resorcinol, in a solvent which is an ester of an aliphatic or aromatic organic acid, preferably methyl benzoate, in the presence of a catalyst chosen from the group of Brönsted acids,
- suspending the red-colored crystals obtained in the preceding step in an anhydrous solvent chosen from the group comprising alcohols such as absolute ethanol, ketones such as acetone, ethers, halogenated solvents, or mixtures thereof,
- acidifying the suspension obtained, by the addition of a strong acid or one of its precursors, chosen from the group comprising sulfuric acid, hydrochloric acid, hydrobromic acid, hydrofluoric acid, hydriodic acid, polyphosphoric acid, pyrophosphate ($P_2O_5$), or mixtures thereof, until yellow-colored crystals are obtained,
- washing the crystals thus obtained with a washing solution chosen from the group comprising water, alcohols, ketones, ethers and halogenated solvents, pure or as a mixture, until red-colored crystals are obtained.

Figure 2:
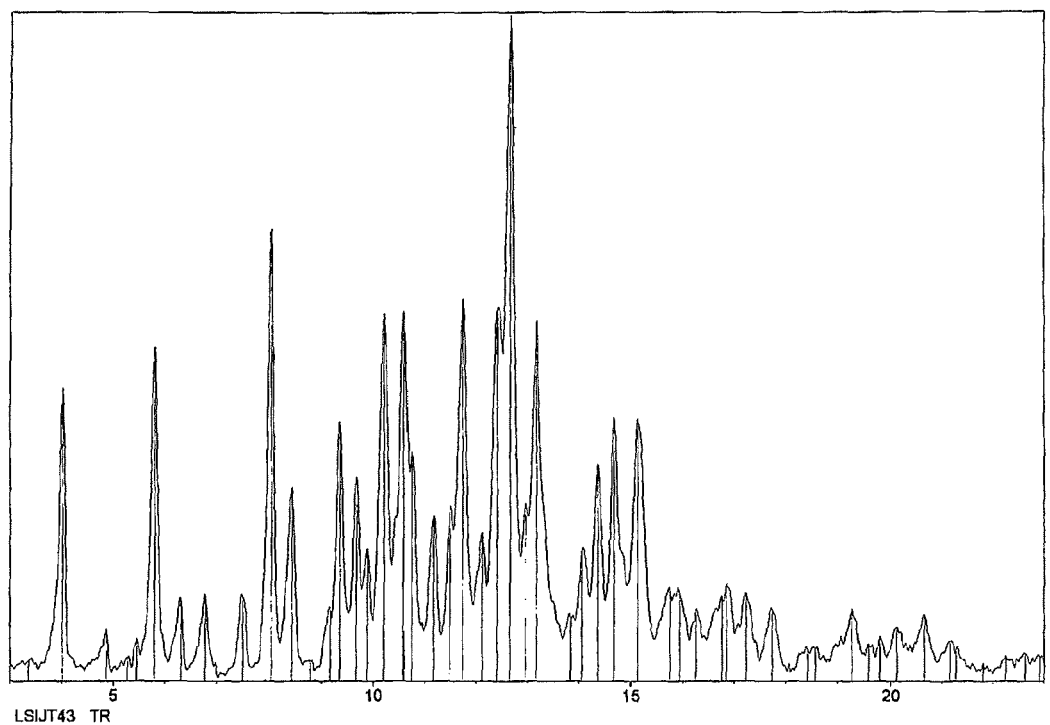
FIG. 2 is a radiocrystallography spectrum of the fluorescein after conversion with acid (yellow).

An X-ray diffraction analysis of the red-colored fluorescein crystals is represented in FIG. 1; an X-ray diffraction analysis of the yellow-colored fluorescein crystals is represented in FIG. 2; these X-ray-diffraction analysis being obtained on the following equipment: Philips 1729 generator, Philips 1050 goniometer, Cu Kα radiation, Gonio acquisition software and Rayon processing software, under the following operating conditions:
Voltage: 40 mV
Intensity: 40 mA
Number of points: 4000
Number of passages: 10
Acquisition period: 250 ms
Start angle (° θ): 3.000
End angle (° θ): 23.000
Standard: silicon According to an advantageous embodiment of the method for preparing fluorescein, the catalyst used for the condensation reaction is the hydrogen sulfate of an alkali metal, preferably potassium hydrogen sulfate or sodium hydrogen sulfate.

According to another advantageous embodiment of the method for preparing fluorescein, the acidification is carried out by sparging gaseous hydrochloric acid into the fluorescein suspension or by the action, on this fluorescein, of hydrochloric acid in solution in an anhydrous organic solvent, preferably chosen from the group comprising alcohols, ketones, ethers and halogenated solvents, used alone or as a mixture, even more preferably isopropanol, absolute ethanol or acetone, pure or as a mixture.

Advantageously, the washing step is carried out with a mixture of water, of ethanol and of acetone.

By means of this method in accordance with the invention, it is possible to prepare fluorescein having a purity of greater than or equal to 99.7%, which provides unquestionable advantages, in particular for pharmaceutical uses in diagnosis, especially in medical imaging or else in the field of biotechnological applications.

The inventors have demonstrated a novel crystallographic form of fluorescein being yellow-colored crystals. This novel crystallographic form is identified by the X-ray diffraction analysis given in FIG. 2, which was determined under the conditions mentioned above.

They have also demonstrated a novel crystallographic form of the following compounds: 4',5'-dihydroxyfluorescein and 4',5'-dimethylfluorescein.

Thus, the invention relates to the yellow-colored fluorescein crystals for which the X-ray diffraction analysis is given in FIG. 2.

Figure 4:
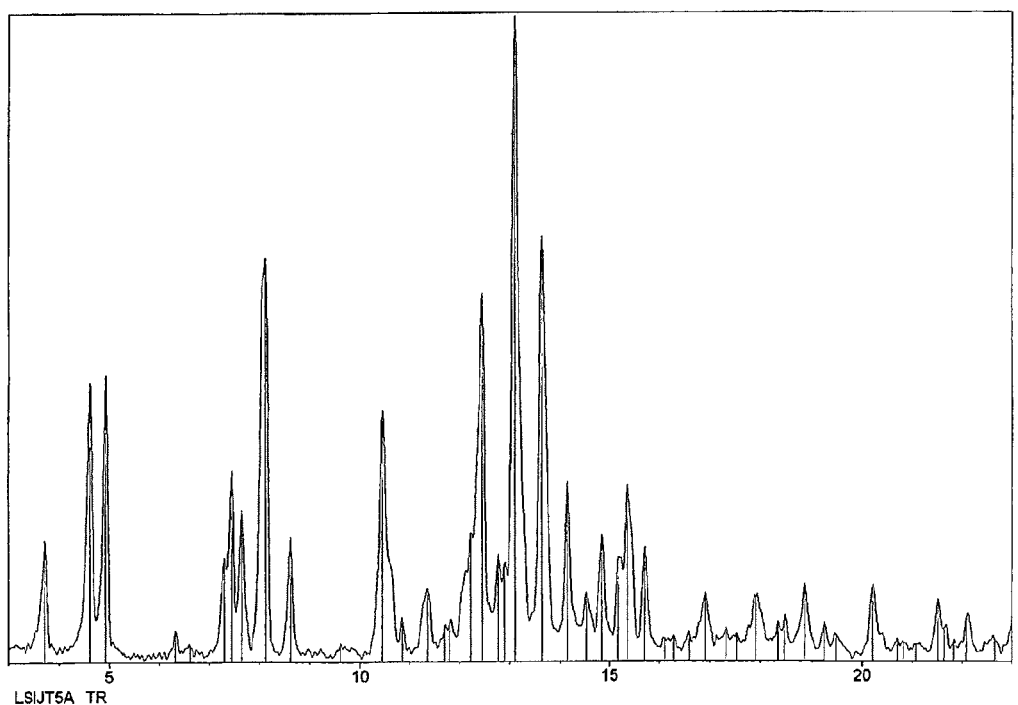
FIG. 4 is a radiocrystallography of the 4',5'-dimethylfluorescein after conversion with acid.
Figure 5:
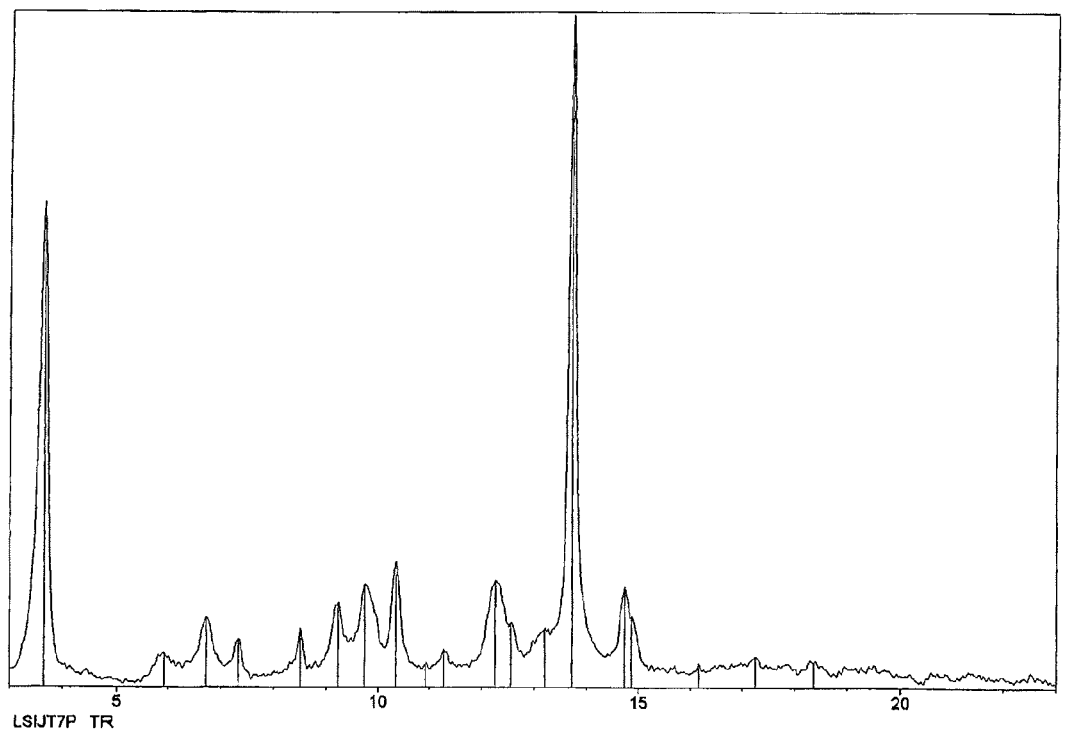
FIG. 5 is a radiocrystallography spectrum of the crude 4',5'-dihydroxyfluorescein.

The invention also relates to the yellow-colored 4',5'-dihydroxyfluorescein crystals for which the X-ray diffraction analysis is given in FIG. 4.

Figure 6:
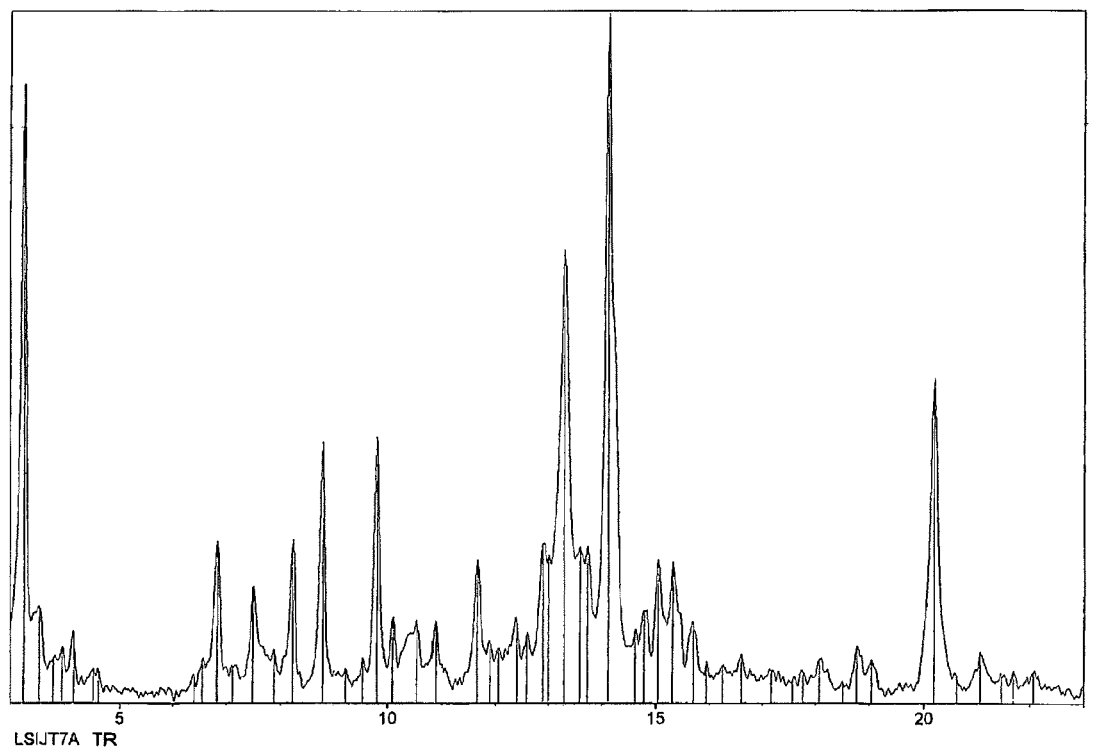
FIG. 6 is a radiocrystallography spectrum of the 4',5',dihydroxyfluorescein after conversion with acid.

It also relates to the dark red-colored 4',5'-dimethylfluorescein crystals for which the X-ray diffraction analysis is given in FIG. 6.

All these spectra were determined with the equipment and under the conditions mentioned above.

The invention will be described in more detail with the aid of the following examples which are not limiting but relate to advantageous embodiments.

EXAMPLES

Example 1

Preparation of High Purity Fluorescein

Synthesis of Fluorescein

A mixture comprising 55 g of resorcinol, 30 g of phthalic anhydride, 2 g of potassium hydrogen sulfate and 500 ml of methyl benzoate is brought to 200° C. for 6 hours. After cooling, the red crystals of crude fluorescein are washed with acetone and dried.

Mass obtained=51.8 g (78%).

These crystals are analyzed by X-ray crystallography under the following operating conditions:
Equipment
Philips 1729 generator
Philips 1050 goniometer
Cu Kα radiation
Gonio acquisition software
Rayon processing software
Conditions
Voltage: 40 mV
Intensity: 40 mA
Number of points: 4000
Number of passages: 10
Acquisition period: 250 ms
Start angle (° θ): 3.000
End angle (° θ): 23.000
Standard: silicon The radiocrystallogram of Table 1 is obtained, for which the peaks are identified below:

| Theta (degrees) | Distance (Å) | % Intensities | Number of counts |
|---|---|---|---|
| 5.3600 | 8.2457 | 18.09 | 647 |
| 5.9500 | 7.4306 | 31.10 | 1112 |
| 6.7000 | 6.6020 | 36.30 | 1298 |
| 8.3750 | 5.2883 | 45.95 | 1643 |
| 9.1050 | 4.8675 | 10.79 | 386 |
| 9.4300 | 4.7012 | 14.09 | 504 |
| 9.9950 | 4.4379 | 8.03 | 287 |
| 10.9150 | 4.0678 | 9.73 | 348 |
| 11.6200 | 3.8241 | 16.41 | 587 |

-continued

| Theta (degrees) | Distance (Å) | % Intensities | Number of counts |
|---|---|---|---|
| 11.7300 | 3.7888 | 5.40 | 193 |
| 12.4200 | 3.5813 | 2.82 | 101 |
| 13.2150 | 3.3694 | 100.00 | 3576 |
| 13.5050 | 3.2983 | 7.47 | 267 |
| 13.8850 | 3.2097 | 79.03 | 2826 |
| 14.9650 | 2.9828 | 5.62 | 201 |
| 15.3100 | 2.9172 | 3.91 | 140 |
| 15.7600 | 2.8359 | 11.69 | 418 |
| 16.0000 | 2.7945 | 8.67 | 310 |
| 16.9100 | 2.6481 | 4.28 | 153 |
| 17.4750 | 2.5650 | 3.97 | 142 |
| 17.8550 | 2.5122 | 3.80 | 136 |
| 18.2300 | 2.4622 | 2.52 | 90 |
| 18.5150 | 2.4256 | 2.96 | 106 |
| 18.8250 | 2.3871 | 5.03 | 180 |
| 19.0800 | 2.3563 | 3.27 | 117 |
| 20.4300 | 2.2066 | 3.05 | 109 |
| 20.6800 | 2.1811 | 4.53 | 162 |
| 20.9300 | 2.1562 | 3.08 | 110 |
| 21.1800 | 2.1319 | 2.38 | 85 |
| 22.9400 | 1.9762 | 4.53 | 162 |

Wavelength: 1.54051 Å

Purification of Crude Fluorescein:

50 g of crude fluorescein obtained in the previous step are stirred into 1000 ml of ethanol/acetone mixture. Concentrated sulfuric acid is added to this mixture, until complete conversion of the red crystals to yellow crystals is obtained.

The yellow crystals obtained are analyzed by X-ray crystallography as above. The X-ray diffraction analysis of Table 2 is obtained, for which the peaks are identified below:

| Theta (degrees) | Distances (Å) | % Intensities | Number of counts |
|---|---|---|---|
| 3.3500 | 13.1813 | 8.55 | 56 |
| 4.0050 | 11.0283 | 47.18 | 309 |
| 4.8550 | 9.1010 | 12.98 | 85 |
| 5.2650 | 8.3940 | 9.01 | 59 |
| 5.4500 | 8.1099 | 11.45 | 75 |
| 5.7900 | 7.6352 | 52.98 | 347 |
| 6.3000 | 7.0193 | 16.95 | 111 |
| 6.7700 | 6.5340 | 17.86 | 117 |
| 7.4900 | 5.9090 | 17.56 | 115 |
| 8.0300 | 5.5140 | 69.77 | 457 |
| 8.4250 | 5.2572 | 33.13 | 217 |
| 8.7800 | 5.0462 | 8.40 | 55 |
| 9.1550 | 4.8411 | 15.88 | 104 |
| 9.3400 | 4.7461 | 42.44 | 278 |
| 9.6550 | 4.5926 | 34.66 | 227 |
| 9.8800 | 4.4891 | 24.43 | 160 |
| 10.1950 | 4.3518 | 57.71 | 378 |
| 10.5800 | 4.1951 | 58.02 | 380 |
| 10.7350 | 4.1352 | 38.17 | 250 |
| 11.1650 | 3.9779 | 28.85 | 189 |
| 11.4800 | 3.8701 | 30.23 | 198 |
| 11.7200 | 3.7919 | 59.85 | 392 |
| 12.1100 | 3.6716 | 26.41 | 173 |
| 12.3950 | 3.5884 | 58.47 | 383 |
| 12.6400 | 3.5200 | 100.00 | 655 |
| 12.9450 | 3.4384 | 30.84 | 202 |
| 13.1550 | 3.3845 | 56.64 | 371 |
| 13.8350 | 3.2211 | 14.66 | 96 |
| 14.0550 | 3.1717 | 24.12 | 158 |
| 14.3550 | 3.1068 | 36.34 | 238 |
| 14.6700 | 3.0415 | 42.90 | 281 |
| 15.1300 | 2.9511 | 42.90 | 281 |
| 15.7500 | 2.8377 | 18.47 | 121 |
| 15.9400 | 2.8047 | 18.17 | 119 |
| 16.2500 | 2.7526 | 15.42 | 101 |
| 16.7550 | 2.6719 | 17.71 | 116 |
| 16.8500 | 2.6573 | 19.39 | 127 |

-continued

| Theta (degrees) | Distances (Å) | % Intensities | Number of counts |
|---|---|---|---|
| 17.2250 | 2.6011 | 18.17 | 119 |
| 17.7300 | 2.5293 | 15.73 | 103 |
| 18.4200 | 2.4377 | 10.23 | 67 |
| 18.5750 | 2.4180 | 10.23 | 67 |
| 19.2650 | 2.3345 | 15.88 | 104 |
| 19.5800 | 2.2984 | 10.84 | 71 |
| 19.8000 | 2.2739 | 11.91 | 78 |
| 20.1150 | 2.2397 | 13.28 | 87 |
| 20.6500 | 2.1841 | 14.81 | 97 |
| 21.1500 | 2.1348 | 11.30 | 74 |
| 21.2750 | 2.1228 | 10.08 | 66 |
| 21.8100 | 2.0732 | 7.94 | 52 |
| 22.2500 | 2.0342 | 9.16 | 60 |
| 22.6250 | 2.0022 | 9.62 | 63 |
| 22.9100 | 1.9786 | 9.01 | 59 |

Wavelength: 1.54051 Å

These crystals are filtered off and then washed with an ethanol/acetone/water (40/40/20) mixture. The washing turns the yellow fluorescein crystals to red fluorescein crystals, which have a higher purity.

Purity by HPLC: 99.8%

Example 2

Preparation of high purity 4',5'-dimethylfluorescein

Synthesis of 4',5'-dimethylfluorescein

A mixture comprising 62 g of 2-methylresorcinol, 30 g of phthalic anhydride, 2 g of potassium hydrogen sulfate and 500 ml of ethyl laurate is brought to 200° C. for 3 hours. After cooling, the crude product is filtered and washed with acetone and then dried. The product obtained is a dark orange powder.

Mass obtained=49.7 g (69%)

Figure 3:
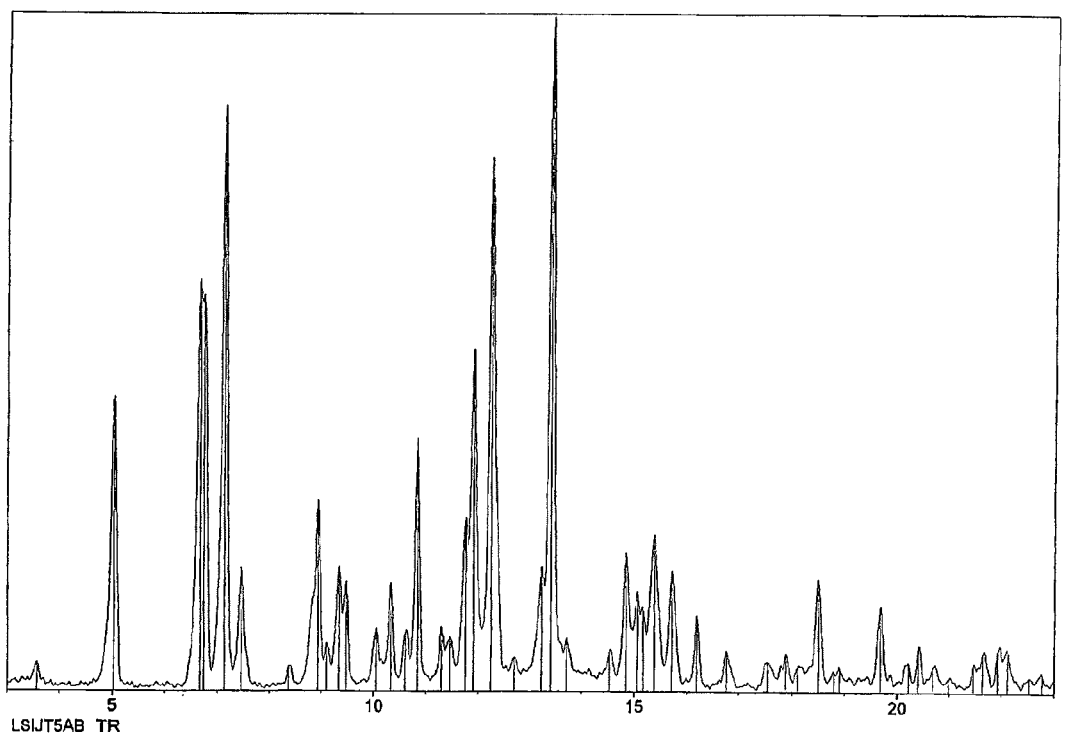
FIG. 3 is a radiocrystallography spectrum of the crude 4',5'-dimethylfluorescein.

These crystals are analyzed by X-ray crystallography in the same way as in example 1. The X-ray diffraction analysis of FIG. 3 is obtained, for which the peaks are identified below.

| Theta (degrees) | Distances (Å) | % Intensities | Number of counts |
|---|---|---|---|
| 3.5700 | 12.3700 | 7.38 | 81 |
| 5.0290 | 8.7938 | 45.49 | 499 |
| 6.6650 | 6.6365 | 62.26 | 683 |
| 6.7400 | 6.5630 | 60.07 | 659 |
| 7.1300 | 6.2057 | 87.24 | 957 |
| 7.4550 | 5.9366 | 20.97 | 230 |
| 8.3700 | 5.2915 | 6.56 | 72 |
| 8.9300 | 4.9621 | 30.63 | 336 |
| 9.0950 | 4.8728 | 10.12 | 111 |
| 9.3300 | 4.7511 | 21.24 | 233 |
| 9.4550 | 4.6889 | 19.05 | 209 |
| 10.0350 | 4.4204 | 12.12 | 133 |
| 10.3250 | 4.2975 | 18.87 | 207 |
| 10.6000 | 4.1873 | 11.49 | 126 |
| 10.8300 | 4.0994 | 39.65 | 435 |
| 11.2900 | 3.9344 | 12.49 | 137 |
| 11.4500 | 3.8801 | 10.85 | 119 |
| 11.7550 | 3.7808 | 28.17 | 309 |
| 11.9050 | 3.7339 | 52.42 | 575 |
| 12.2550 | 3.6288 | 79.95 | 877 |
| 12.7050 | 3.5023 | 8.11 | 89 |
| 13.2400 | 3.3631 | 21.15 | 232 |
| 13.4200 | 3.3188 | 100.00 | 1097 |
| 13.7100 | 3.2499 | 10.85 | 119 |
| 14.5250 | 3.0712 | 8.84 | 97 |
| 14.8350 | 3.0084 | 23.25 | 255 |

-continued

| Theta (degrees) | Distances (Å) | % Intensities | Number of counts |
|---|---|---|---|
| 15.0550 | 2.9654 | 17.59 | 193 |
| 15.1550 | 2.9463 | 15.13 | 166 |
| 15.3650 | 2.9070 | 25.80 | 283 |
| 15.7050 | 2.8456 | 20.51 | 225 |
| 16.1900 | 2.7625 | 14.13 | 155 |
| 16.7550 | 2.6719 | 9.02 | 99 |
| 17.5400 | 2.5558 | 7.47 | 82 |
| 17.8850 | 2.5081 | 8.75 | 96 |
| 18.1050 | 2.4786 | 6.75 | 74 |
| 18.4900 | 2.4288 | 19.51 | 214 |
| 18.7950 | 2.3907 | 6.11 | 67 |
| 18.8900 | 2.3791 | 6.84 | 75 |
| 19.6800 | 2.2872 | 15.50 | 170 |
| 20.2100 | 2.2296 | 7.38 | 81 |
| 20.3950 | 2.2103 | 9.66 | 106 |
| 20.6800 | 2.1811 | 6.84 | 75 |
| 20.9950 | 2.1498 | 5.38 | 59 |
| 21.4650 | 2.1049 | 7.11 | 78 |
| 21.6500 | 2.0878 | 8.84 | 97 |
| 21.9350 | 2.0620 | 9.21 | 101 |
| 22.1250 | 2.0451 | 9.02 | 99 |
| 22.5300 | 2.0102 | 5.47 | 60 |
| 22.7850 | 1.9889 | 5.93 | 65 |

Wavelength: 1.54051 Å

Purification of 4',5'-dimethylfluorescein 40 g of crude 4',5'-dimethylfluorescein are added to 800 ml of ethanol/acetone mixture. Concentrated sulfuric acid is added to this mixture, until complete conversion of dark orange-colored crystals to yellow-colored crystals is obtained.

The yellow crystals obtained are analyzed by X-ray crystallography as above. The X-ray diffraction analysis of Table 4 is obtained, for which the peaks are identified below.

| Theta (degrees) | Distances (Å) | % Intensities | Number of counts |
|---|---|---|---|
| 3.7050 | 11.9199 | 22.22 | 172 |
| 4.6150 | 9.5732 | 45.61 | 353 |
| 4.9300 | 8.9629 | 46.77 | 362 |
| 6.3300 | 6.9861 | 8.53 | 66 |
| 6.6150 | 6.6864 | 6.20 | 48 |
| 7.3000 | 6.0619 | 19.51 | 151 |
| 7.4500 | 5.9405 | 32.56 | 252 |
| 7.6500 | 5.7861 | 26.61 | 206 |
| 8.1250 | 5.4499 | 64.21 | 497 |
| 8.6300 | 5.1332 | 22.48 | 174 |
| 9.5950 | 4.6211 | 6.59 | 51 |
| 10.4450 | 4.2487 | 41.34 | 320 |
| 10.8500 | 4.0919 | 10.21 | 79 |
| 11.3550 | 3.9122 | 14.60 | 113 |
| 11.7000 | 3.7983 | 9.17 | 71 |
| 11.7950 | 3.7682 | 9.30 | 72 |
| 12.2250 | 3.6375 | 23.13 | 179 |
| 12.4500 | 3.5728 | 58.79 | 455 |
| 12.7650 | 3.4861 | 19.90 | 154 |
| 12.8950 | 3.4515 | 18.60 | 144 |
| 13.1000 | 3.3984 | 100.00 | 774 |
| 13.6350 | 3.2675 | 67.44 | 522 |
| 14.1400 | 3.1530 | 30.75 | 238 |
| 14.5250 | 3.0712 | 14.08 | 109 |
| 14.8400 | 3.0074 | 22.74 | 176 |
| 15.1750 | 2.9425 | 19.38 | 150 |
| 15.3500 | 2.9098 | 30.23 | 234 |
| 15.6950 | 2.8474 | 20.93 | 162 |
| 16.0950 | 2.7784 | 7.24 | 56 |
| 16.2850 | 2.7468 | 7.49 | 58 |
| 16.5950 | 2.6969 | 8.01 | 62 |
| 16.9100 | 2.6481 | 14.08 | 109 |
| 17.3200 | 2.5873 | 8.66 | 67 |
| 17.5400 | 2.5558 | 7.88 | 61 |
| 17.9150 | 2.5040 | 13.31 | 103 |
| 18.3550 | 2.4460 | 9.69 | 75 |
| 18.4800 | 2.4300 | 10.59 | 82 |
| 18.8600 | 2.3828 | 15.37 | 119 |
| 19.2350 | 2.3380 | 9.43 | 73 |
| 19.4850 | 2.3092 | 7.75 | 60 |
| 20.2100 | 2.2296 | 14.99 | 116 |
| 20.7100 | 2.1781 | 7.11 | 55 |
| 20.8350 | 2.1656 | 6.59 | 51 |
| 21.0850 | 2.1411 | 6.33 | 49 |
| 21.5250 | 2.0993 | 12.92 | 100 |
| 21.6500 | 2.0878 | 8.79 | 68 |
| 21.8400 | 2.0705 | 6.98 | 54 |
| 22.0900 | 2.0482 | 10.34 | 80 |
| 226550 | 1.9997 | 7.11 | 55 |

Wavelength 1.54051 Å

After filtration and recrystallization from an acetone/water mixture or washing in ethanol/acetone/water, the yellow-colored crystals turn to dark orange-colored crystals.

Example 3

Preparation of 4',5'-dihydroxyfluorescein

Synthesis of 4',5'-dihydroxyfluorescein

A mixture comprising 63 g of pyrogallol, 30 g of phthalic anhydride, 2 g of potassium hydrogen sulfate and 500 ml of ethyl myristate is brought to 200° C. for 3 hours. After cooling, the crude product is filtered and washed with acetone and then dried. The product obtained is a grayish-brown- or anthracite-colored powder.

Mass obtained=43.5 g (59.7%)

The crystals obtained are analyzed by X-ray crystallography as above. The X-ray diffraction analysis of Table 5 is obtained, the peaks of which are identified below.

| Theta (degrees) | Distances (Å) | % Intensities | Number of counts |
|---|---|---|---|
| 3.6450 | 12.1158 | 73.08 | 980 |
| 5.9200 | 7.4681 | 8.13 | 109 |
| 6.7200 | 6.5824 | 13.35 | 179 |
| 7.3350 | 6.0331 | 10.29 | 138 |
| 8.5050 | 5.2081 | 11.78 | 158 |
| 9.2300 | 4.8021 | 15.59 | 209 |
| 9.7400 | 4.5529 | 18.20 | 244 |
| 10.3400 | 4.2914 | 21.40 | 287 |
| 10.9150 | 4.0678 | 6.71 | 90 |
| 11.2600 | 3.9447 | 8.80 | 118 |
| 12.2550 | 3.6288 | 18.64 | 250 |
| 12.5550 | 3.5434 | 12.75 | 171 |
| 13.2000 | 3.3731 | 11.86 | 159 |
| 13.7200 | 3.2476 | 100.00 | 1341 |
| 14.7150 | 3.0324 | 17.75 | 238 |
| 14.8600 | 3.0034 | 13.57 | 182 |
| 16.1600 | 2.7675 | 6.79 | 91 |
| 17.2550 | 2.5967 | 7.83 | 105 |
| 18.3550 | 2.4460 | 6.86 | 92 |

Wavelength: 1.54051 Å

Purification of 4',5'-dihydroxyfluorescein 40 g of crude 4',5'-dihydroxyfluorescein are added to 800 ml of ethanol/acetone mixture. Concentrated sulfuric acid is added to this mixture, until complete conversion of grayish-brown- or anthracite-colored crystals to reddish-brown- or mahogany-colored crystals is obtained.

The crystals obtained are analyzed by X-ray crystallography as above. The X-ray diffraction analysis of Table 6 is obtained, for which the peaks are identified below:

| Theta (degrees) | Distances (Å) | % Intensities | Number of counts |
|---|---|---|---|
| 3.2500 | 13.5865 | 90.53 | 526 |
| 3.5350 | 12.4923 | 18.76 | 109 |
| 3.7850 | 11.6683 | 11.70 | 68 |
| 3.9450 | 11.1958 | 13.25 | 77 |
| 4.1650 | 10.6053 | 15.15 | 88 |
| 4.5400 | 9.7310 | 10.33 | 60 |
| 4.6350 | 9.5319 | 10.15 | 59 |
| 6.3950 | 6.9154 | 9.29 | 54 |
| 6.5500 | 6.7525 | 11.53 | 67 |
| 6.8200 | 6.4863 | 27.71 | 161 |
| 7.1150 | 6.2187 | 10.50 | 61 |
| 7.4800 | 5.9168 | 21.51 | 125 |
| 7.8700 | 5.6253 | 12.91 | 75 |
| 8.2200 | 5.3874 | 27.88 | 162 |
| 8.7800 | 5.0462 | 41.48 | 241 |
| 9.2200 | 4.8073 | 10.15 | 59 |
| 9.5350 | 4.6499 | 11.70 | 68 |
| 9.7950 | 4.5276 | 42.17 | 245 |
| 10.1000 | 4.3923 | 17.21 | 100 |
| 10.5400 | 4.2108 | 16.70 | 97 |
| 10.8850 | 4.0789 | 16.52 | 96 |
| 11.6500 | 3.8144 | 25.13 | 146 |
| 11.8900 | 3.7385 | 13.60 | 79 |
| 12.0450 | 3.6911 | 13.08 | 76 |
| 12.3900 | 3.5898 | 16.52 | 96 |
| 12.5800 | 3.5365 | 14.80 | 86 |
| 12.8750 | 3.4568 | 27.37 | 159 |
| 12.9950 | 3.4254 | 25.82 | 150 |
| 13.2900 | 3.3507 | 67.64 | 393 |
| 13.5750 | 3.2816 | 27.02 | 157 |
| 13.7150 | 3.2488 | 27.02 | 157 |
| 14.1100 | 3.1596 | 100.00 | 581 |
| 14.6200 | 3.0516 | 15.66 | 91 |
| 14.7750 | 3.0203 | 18.24 | 106 |
| 15.0400 | 2.9683 | 25.13 | 146 |
| 15.3050 | 2.9181 | 24.78 | 144 |
| 15.6850 | 2.8491 | 16.35 | 95 |
| 15.9400 | 2.8047 | 11.02 | 64 |
| 16.2500 | 2.7526 | 10.67 | 62 |
| 16.5950 | 2.6969 | 12.22 | 71 |
| 17.1650 | 2.6099 | 9.81 | 57 |
| 17.5700 | 2.5516 | 8.78 | 51 |
| 17.7600 | 2.5252 | 9.81 | 57 |
| 18.0750 | 2.4826 | 11.36 | 66 |
| 18.5150 | 2.4256 | 8.43 | 49 |
| 18.7650 | 2.3944 | 13.08 | 76 |
| 19.0450 | 2.3605 | 11.36 | 66 |
| 20.1950 | 2.2312 | 50.09 | 291 |
| 20.6150 | 2.1877 | 9.12 | 53 |
| 21.0550 | 2.1440 | 12.56 | 73 |
| 21.4650 | 2.1049 | 9.29 | 54 |
| 21.6850 | 2.0846 | 9.98 | 58 |
| 22.0600 | 2.0509 | 9.81 | 57 |

Wavelength: 1.54051 Å

After filtration and washing in water, the reddish-brown-or mahogany-colored crystals turn to grayish brown-or anthracite-colored crystals.

The invention claimed is:

1. A yellow-colored fluorescein crystal having a X-ray diffraction spectrum at a wave length of 1.54051 Å characterized by the following peaks:

| Theta (degrees) | Distances (Å) | % Intensities | Number of counts |
|---|---|---|---|
| 3.3500 | 13.1813 | 8.55 | 56 |
| 4.0050 | 11.0283 | 47.18 | 309 |
| 4.8550 | 9.1010 | 12.98 | 85 |
| 5.2650 | 8.3940 | 9.01 | 59 |
| 5.4500 | 8.1099 | 11.45 | 75 |
| 5.7900 | 7.6352 | 52.98 | 347 |
| 6.3000 | 7.0193 | 16.95 | 111 |
| 6.7700 | 6.5340 | 17.86 | 117 |
| 7.4900 | 5.9090 | 17.56 | 115 |
| 8.0300 | 5.5140 | 69.77 | 457 |
| 8.4250 | 5.2572 | 33.13 | 217 |
| 8.7800 | 5.0462 | 8.40 | 55 |
| 9.1550 | 4.8411 | 15.88 | 104 |
| 9.3400 | 4.7461 | 42.44 | 278 |
| 9.6550 | 4.5926 | 34.66 | 227 |
| 9.8800 | 4.4891 | 24.43 | 160 |
| 10.1950 | 4.3518 | 57.71 | 378 |
| 10.5800 | 4.1951 | 58.02 | 380 |
| 10.7350 | 4.1352 | 38.17 | 250 |
| 11.1650 | 3.9779 | 28.85 | 189 |
| 11.4800 | 3.8701 | 30.23 | 198 |
| 11.7200 | 3.7919 | 59.85 | 392 |
| 12.1100 | 3.6716 | 26.41 | 173 |
| 12.3950 | 3.5884 | 58.47 | 383 |
| 12.6400 | 3.5200 | 100.00 | 655 |
| 12.9450 | 3.4384 | 30.84 | 202 |
| 13.1550 | 3.3845 | 56.64 | 371 |
| 13.8350 | 3.2211 | 14.66 | 96 |
| 14.0550 | 3.1717 | 24.12 | 158 |
| 14.3550 | 3.1068 | 36.34 | 238 |
| 14.6700 | 3.0415 | 42.90 | 281 |
| 15.1300 | 2.9511 | 42.90 | 281 |
| 15.7500 | 2.8377 | 18.47 | 121 |
| 15.9400 | 2.8047 | 18.17 | 119 |
| 16.2500 | 2.7526 | 15.42 | 101 |
| 16.7550 | 2.6719 | 17.71 | 116 |
| 16.8500 | 2.6573 | 19.39 | 127 |
| 17.2250 | 2.6011 | 18.17 | 119 |
| 17.7300 | 2.5293 | 15.73 | 103 |
| 18.4200 | 2.4377 | 10.23 | 67 |
| 18.5750 | 2.4180 | 10.23 | 67 |
| 19.2650 | 2.3345 | 15.88 | 104 |
| 19.5800 | 2.2984 | 10.84 | 71 |
| 19.8000 | 2.2739 | 11.91 | 78 |
| 20.1150 | 2.2397 | 13.28 | 87 |
| 20.6500 | 2.1841 | 14.81 | 97 |
| 21.1500 | 2.1348 | 11.30 | 74 |
| 21.2750 | 2.1228 | 10.08 | 66 |
| 21.8100 | 2.0732 | 7.94 | 52 |
| 22.2500 | 2.0342 | 9.16 | 60 |
| 22.6250 | 2.0022 | 9.62 | 63 |
| 22.9100 | 1.9786 | 9.01 | 59. |

2. A yellow-colored 4',5'-dimethylfluorescein crystal having the X-ray diffraction spectrum at a wave length of 1.54051 Å characterized by the following peaks:

| Theta (degrees) | Distances (Å) | % Intensities | Number of counts |
|---|---|---|---|
| 3.7050 | 11.9199 | 22.22 | 172 |
| 4.6150 | 9.5732 | 45.61 | 353 |
| 4.9300 | 8.9629 | 46.77 | 362 |
| 6.3300 | 6.9861 | 8.53 | 66 |
| 6.6150 | 6.6864 | 6.20 | 48 |
| 7.3000 | 6.0619 | 19.51 | 151 |
| 7.4500 | 5.9405 | 32.56 | 252 |
| 7.6500 | 5.7861 | 26.61 | 206 |
| 8.1250 | 5.4499 | 64.21 | 497 |

-continued

| Theta (degrees) | Distances (Å) | % Intensities | Number of counts |
| --- | --- | --- | --- |
| 8.6300 | 5.1332 | 22.48 | 174 |
| 9.5950 | 4.6211 | 6.59 | 51 |
| 10.4450 | 4.2487 | 41.34 | 320 |
| 10.8500 | 4.0919 | 10.21 | 79 |
| 11.3550 | 3.9122 | 14.60 | 113 |
| 11.7000 | 3.7983 | 9.17 | 71 |
| 11.7950 | 3.7682 | 9.30 | 72 |
| 12.2250 | 3.6375 | 23.13 | 179 |
| 12.4500 | 3.5728 | 58.79 | 455 |
| 12.7650 | 3.4861 | 19.90 | 154 |
| 12.8950 | 3.4515 | 18.60 | 144 |
| 13.1000 | 3.3984 | 100.00 | 774 |
| 13.6350 | 3.2675 | 67.44 | 522 |
| 14.1400 | 3.1530 | 30.75 | 238 |
| 14.5250 | 3.0712 | 14.08 | 109 |
| 14.8400 | 3.0074 | 22.74 | 176 |
| 15.1750 | 2.9425 | 19.38 | 150 |
| 15.3500 | 2.9098 | 30.23 | 234 |
| 15.6950 | 2.8474 | 20.93 | 162 |
| 16.0950 | 2.7784 | 7.24 | 56 |
| 16.2850 | 2.7468 | 7.49 | 58 |
| 16.5950 | 2.6969 | 8.01 | 62 |
| 16.9100 | 2.6481 | 14.08 | 109 |
| 17.3200 | 2.5873 | 8.66 | 67 |
| 17.5400 | 2.5558 | 7.88 | 61 |
| 17.9150 | 2.5040 | 13.31 | 103 |
| 18.3550 | 2.4460 | 9.69 | 75 |
| 18.4800 | 2.4300 | 10.59 | 82 |
| 18.8600 | 2.3828 | 15.37 | 119 |
| 19.2350 | 2.3380 | 9.43 | 73 |
| 19.4850 | 2.3092 | 7.75 | 60 |
| 20.2100 | 2.2296 | 14.99 | 116 |
| 20.7100 | 2.1781 | 7.11 | 55 |
| 20.8350 | 2.1656 | 6.59 | 51 |
| 21.0850 | 2.1411 | 6.33 | 49 |
| 21.5250 | 2.0993 | 12.92 | 100 |
| 21.6500 | 2.0878 | 8.79 | 68 |
| 21.8400 | 2.0705 | 6.98 | 54 |
| 22.0900 | 2.0482 | 10.34 | 80 |
| 226550 | 1.9997 | 7.11 | 55. |

3. A reddish-brown- or mahogany-colored 4',5'-dihydroxyfluorescein crystal having the X-ray diffraction spectrum at a wave length of 1.54051 Å characterized by the following peaks:

| Theta (degrees) | Distances (Å) | % Intensities | Number of counts |
| --- | --- | --- | --- |
| 3.2500 | 13.5865 | 90.53 | 526 |
| 3.5350 | 12.4923 | 18.76 | 109 |
| 3.7850 | 11.6683 | 11.70 | 68 |
| 3.9450 | 11.1958 | 13.25 | 77 |
| 4.1650 | 10.6053 | 15.15 | 88 |
| 4.5400 | 9.7310 | 10.33 | 60 |
| 4.6350 | 9.5319 | 10.15 | 59 |
| 6.3950 | 6.9154 | 9.29 | 54 |
| 6.5500 | 6.7525 | 11.53 | 67 |
| 6.8200 | 6.4863 | 27.71 | 161 |
| 7.1150 | 6.2187 | 10.50 | 61 |
| 7.4800 | 5.9168 | 21.51 | 125 |
| 7.8700 | 5.6253 | 12.91 | 75 |
| 8.2200 | 5.3874 | 27.88 | 162 |
| 8.7800 | 5.0462 | 41.48 | 241 |
| 9.2200 | 4.8073 | 10.15 | 59 |
| 9.5350 | 4.6499 | 11.70 | 68 |
| 9.7950 | 4.5276 | 42.17 | 245 |
| 10.1000 | 4.3923 | 17.21 | 100 |
| 10.5400 | 4.2108 | 16.70 | 97 |
| 10.8850 | 4.0789 | 16.52 | 96 |
| 11.6500 | 3.8144 | 25.13 | 146 |
| 11.8900 | 3.7385 | 13.60 | 79 |
| 12.0450 | 3.6911 | 13.08 | 76 |
| 12.3900 | 3.5898 | 16.52 | 96 |
| 12.5800 | 3.5365 | 14.80 | 86 |
| 12.8750 | 3.4568 | 27.37 | 159 |
| 12.9950 | 3.4254 | 25.82 | 150 |
| 13.2900 | 3.3507 | 67.64 | 393 |
| 13.5750 | 3.2816 | 27.02 | 157 |
| 13.7150 | 3.2488 | 27.02 | 157 |
| 14.1100 | 3.1596 | 100.00 | 581 |
| 14.6200 | 3.0516 | 15.66 | 91 |
| 14.7750 | 3.0203 | 18.24 | 106 |
| 15.0400 | 2.9683 | 25.13 | 146 |
| 15.3050 | 2.9181 | 24.78 | 144 |
| 15.6850 | 2.8491 | 16.35 | 95 |
| 15.9400 | 2.8047 | 11.02 | 64 |
| 16.2500 | 2.7526 | 10.67 | 62 |
| 16.5950 | 2.6969 | 12.22 | 71 |
| 17.1650 | 2.6099 | 9.81 | 57 |
| 17.5700 | 2.5516 | 8.78 | 51 |
| 17.7600 | 2.5252 | 9.81 | 57 |
| 18.0750 | 2.4826 | 11.36 | 66 |
| 18.5150 | 2.4256 | 8.43 | 49 |
| 18.7650 | 2.3944 | 13.08 | 76 |
| 19.0450 | 2.3605 | 11.36 | 66 |
| 20.1950 | 2.2312 | 50.09 | 291 |
| 20.6150 | 2.1877 | 9.12 | 53 |
| 21.0550 | 2.1440 | 12.56 | 73 |
| 21.4650 | 2.1049 | 9.29 | 54 |
| 21.6850 | 2.0846 | 9.98 | 58 |
| 22.0600 | 2.0509 | 9.81 | 57. |

4. A pharmaceutical composition comprising the fluorescein of claim 1 and a pharmaceutically acceptable excipient.

5. A labelling composition comprising the fluorescein of claim 1.

6. A method for medical imaging a patient comprising administering to said patient a composition comprising the fluorescein of claim 1, and then collecting an image of said patient.

7. A method of imaging a biological sample in vitro comprising contacting the sample with a fluorescein of claim 1, then collecting an image of said sample.

8. A method of diagnosing a patient suffering from, or at risk of developing, vascular pathologies of the retina or of the choroid comprising administering to said patient a composition comprising the fluorescein of claim 1, collecting an image of said retina or choroid, and assessing the image.

9. A pharmaceutical composition for diagnosis comprising the 4',5'-dimethylfluorescein of claim 2 and a pharmaceutically acceptable excipient.

10. A labelling composition comprising the 4',5'-dimethylfluorescein of claim 2.

11. A method for medical imaging a patient comprising administering to said patient a composition comprising the 4',5'-dimethylfluorescein of claim 2, and then collecting an image of said patient.

12. A method of imaging a biological sample in vitro comprising contacting the sample with a 4',5'-dimethylfluorescein of claim 2, then collecting an image of said sample.

13. A method of diagnosing a patient suffering from, or at risk of developing, vascular pathologies of the retina or of the choroid comprising administering to said patient a composition comprising the 4',5'-dimethylfluorescein of claim 2, collecting an image of said retina or choroid, and assessing the image.

14. A pharmaceutical composition for diagnosis comprising the 4',5'-dihydroxyfluorescein of claim 3 and a pharmaceutically acceptable excipient.

15. A labelling composition comprising the 4',5'-dihydroxyfluorescein of claim 3.

16. A method for medical imaging a patient comprising administering to said patient a composition comprising the 4',5'-dihydroxyfluorescein of claim 3, and then collecting an image of said patient.

17. A method of imaging a biological sample in vitro comprising contacting the sample with a 4',5'-dihydroxyfluorescein of claim 3, then collecting an image of said sample.

18. A method of diagnosing a patient suffering from, or at risk of developing, vascular pathologies of the retina or of the choroid comprising administering to said patient a composition comprising the 4',5'-dihydroxyfluorescein of claim 3, collecting an image of said retina or choroid, and assessing the image.

* * * * *